(12) United States Patent
Poppe et al.

(10) Patent No.: US 9,858,489 B2
(45) Date of Patent: Jan. 2, 2018

(54) DEVICE FOR ESTIMATING THE ALERTNESS OF A DRIVER

(71) Applicant: GM GLOBAL TECHNOLOGY OPERATIONS LLC, Detroit, MI (US)

(72) Inventors: Stefan Poppe, Darmstadt (DE); Bjoern Frank, Wiesbaden (DE)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 342 days.

(21) Appl. No.: 14/493,135

(22) Filed: Sep. 22, 2014

(65) Prior Publication Data

US 2015/0085124 A1 Mar. 26, 2015

(30) Foreign Application Priority Data

Sep. 21, 2013 (DE) .................... 20 2013 008 392 U

(51) Int. Cl.
| | |
|---|---|
| A61B 5/18 | (2006.01) |
| B60K 28/06 | (2006.01) |
| G08C 21/00 | (2006.01) |
| G06K 9/00 | (2006.01) |
| G08B 21/06 | (2006.01) |
| B60W 40/08 | (2012.01) |

(52) U.S. Cl.
CPC ............ *G06K 9/00845* (2013.01); *A61B 5/18* (2013.01); *B60K 28/06* (2013.01); *G08B 21/06* (2013.01); *G08C 21/00* (2013.01); *B60W 2040/0827* (2013.01)

(58) Field of Classification Search
CPC ...... G06K 9/00845; A61B 5/18; B60K 28/06; G08C 21/00; G08B 21/06
See application file for complete search history.

(56) References Cited

U.S. PATENT DOCUMENTS

| | | | | |
|---|---|---|---|---|
| 2008/0059571 | A1* | 3/2008 | Khoo ..................... | G06Q 30/02 709/203 |
| 2011/0285525 | A1* | 11/2011 | Ishibashi ................ | G09F 21/04 340/461 |
| 2012/0021540 | A1 | 1/2012 | Takahashi et al. | |
| 2012/0215403 | A1 | 8/2012 | Tengler et al. | |
| 2014/0211319 | A1* | 7/2014 | Park ....................... | G02B 27/01 359/630 |
| 2015/0029013 | A1* | 1/2015 | Osornio Lopez ...... | B60K 35/00 340/438 |

FOREIGN PATENT DOCUMENTS

| | | |
|---|---|---|
| DE | 10039795 A1 | 3/2002 |
| DE | 10326358 A1 | 12/2004 |
| DE | 102008004908 A1 | 7/2009 |
| DE | 102008038816 A1 | 2/2010 |
| DE | 102009041187 A1 | 2/2011 |
| DE | 102011079703 A1 | 1/2013 |
| DE | 102011084887 A1 | 4/2013 |

* cited by examiner

*Primary Examiner* — Nam Pham
(74) *Attorney, Agent, or Firm* — Lorenz & Kopf, LLP

(57) ABSTRACT

A system and method for estimating the alertness of the driver in a moving vehicle is disclosed. A display instrument is switched over in order to display a message relating to the movement of the vehicle. An eye movement of the driver in reaction to the switch-over is detected. The driver's alertness is assessed on the basis of the detected eye movement.

20 Claims, 2 Drawing Sheets

DEVICE FOR ESTIMATING THE ALERTNESS OF A DRIVER

CROSS REFERENCE TO RELATED APPLICATION

This application claims priority to German Patent Application No. 202013008392.1 filed Sep. 21, 2013, which is incorporated herein by reference in its entirety.

TECHNICAL FIELD

The technical field relates to a device for estimating the alertness of a driver in a motor vehicle.

BACKGROUND

DE102008004908A1 discloses a motor vehicle, in which a control device issues a stimulus signal perceptible to the driver, ascertains the reaction time of the driver to the stimulus signal and on the basis of this reaction time or the absence of a reaction assesses the alertness of the driver. Examples for possible stimulus signals are listed, such as a reduction in vehicle speed, a change in the interval duration of a windscreen wiper system, a change in the loudness of an audio system, a change in the illumination of color or brightness of a display instrument, etc. The stimulus signal must not have a direct influence upon the traffic safety of the motor vehicle. A disadvantage of this system consists in that an arbitrary deviation of the vehicle from the defaults set by the driver, be it in the form of a reduction in speed or a windscreen wiper interval, is perceived by the driver as annoying if not appropriate to the current traffic situation, and accepted without reaction if appropriate. Therefore there exists the possibility that the assessment of driver alertness based on such stimulus signals is perceived as an annoying interference and paternalism, or, in case the driver does not feel the need to correct the influence of the stimulus signal upon the vehicle and therefore ignores it, that alertness may be inaccurately assessed.

SUMMARY

In accordance with an implementation of the present disclosure a method for estimating driver alertness is proposed which presents only a small risk that the driver will perceive this as an annoying interference or ignore it as being irrelevant.

According to one implementation of the present disclosure the requirement is met by a device for estimating the alertness of a driver in a moving vehicle having a driver unit for a display instrument for switching over the display instrument in reaction to a message relating to the movement of the vehicle, and an evaluation unit for assessing the alertness of the driver on the basis of images of at least his eyes. Such a device, i.e. its driver and evaluation unit, can be respectively implemented by a suitably programmed computer. The device may include a camera for detecting an eye movement of the driver in reaction to the switch-over.

According to another implementation of the present disclosure the requirement is met by a computer program product having instructions which when executed on a computer enable the same, at least in its capacity as a driver unit and additionally possibly as an evaluation unit, to work in the above-described device, and/or to execute a method for estimating the alertness of the driver in a moving vehicle, the method including switch-over of a display instrument in order to display a message relating to the movement of the vehicle, detecting an eye movement of the driver in reaction to the switch-over, and assessing the alertness on the basis of the detected eye movement.

When the offered stimulus signal consists in displaying a message, then an interference with the vehicle movement, which might be perceived by the driver as paternalism, is not necessary. Since the displaying of information does not necessarily trigger a corrective reaction by the driver, it is not possible to use this corrective reaction and possible time span between stimulus signal and corrective reaction as a basis for assessing the alertness of the driver. What can be assessed, however, is a possible eye movement of the driver when he looks at the display instrument and takes note of the message. The eye movement is therefore a suitable criterion for assessing the alertness.

So as to ensure that the driver does not ignore the messages on the display instrument, these should be variable, i.e. the driver should not be able to predict the subsequent message from one or more of the noted messages. This can, for example, be achieved by the following preparatory actions: assigning priorities to the different messages, and selecting the message with the highest priority as the message to be displayed.

So as to ensure that a message once issued is not repeated, provision may be made for the priority of the respectively displayed message to be lowered.

In a counter move the priority of at least one of the messages not previously issued may be incremented in order to raise the probability that for a next execution this message is displayed. Alternatively the priority of at least one of the messages can be increased proportionally to the time elapsed in order to achieve the fact that the respective message is displayed after a certain waiting time.

As a further alternative, with respect to a message which is related to an object external to the vehicle, consideration could be given to increase the priority of the message as the distance between the vehicle and the object decreases, in order to ensure in this way that the driver is alerted to this object in good time.

If one of the messages is related to an operating parameter of the vehicle a further meaningful possibility would be to increase the priority of the message if the distance of the operating parameter from a threshold decreases or the operating parameter exceeds this threshold value.

The different possibilities for changing the priority may be applied in an identical method for different types of messages, respectively.

So as not to irritate the driver by displaying a plurality of messages provision may be made for a minimum waiting time to be adhered to between two repetitions of displayed messages.

There may be messages, such as warnings to beware of other traffic participants or obstacles on or next to the carriageway, which may be obsolete after a short time so that adherence to a minimum waiting time is not meaningful for these. Therefore the messages can be alternatively divided into at least two different relevance classes, wherein message display is repeated as soon as the priority of a message of the first relevance class has exceeded a threshold value, or soon as a minimum waiting time has elapsed since the previous display. Messages of the first relevance class can thus be displayed quickly and at any time, whilst other messages must adhere to the minimum waiting time.

Further provision may be made message display to be repeated after a maximum waiting time has passed, respectively, in order to ensure that the period of time passed is not too long without the alertness of the driver being assessed. After the maximum waiting time has passed therefore, the message with the then highest priority is issued, respectively, independently of how high the priority is. Before the maximum waiting time has passed message display may be repeated if the priority of one of the messages exceeds a threshold value. In general this will be the message with the highest priority, which is then also issued.

The computer program product may be configured as a data carrier on which the instructions have been recorded which enable a computer to operate in the above-described manner.

A yet further subject of the present disclosure is an electronic estimating unit for estimating the alertness of a driver in a moving vehicle, with means for switching a display instrument over in order to display a message relating to the movement of the motor vehicle, means for detecting an eye movement of the driver in reaction to the switch-over, and means for assessing the alertness on the basis of a detected eye movement.

BRIEF DESCRIPTION OF THE DRAWINGS

The present disclosure will hereinafter be described in conjunction with the following drawing figures, wherein like numerals denote like elements.

DETAILED DESCRIPTION

The following detailed description is merely exemplary in nature and is not intended to limit the present disclosure or the application and uses of the present disclosure. Furthermore, there is no intention to be bound by any theory presented in the preceding background or the following detailed description.

Figure 1:
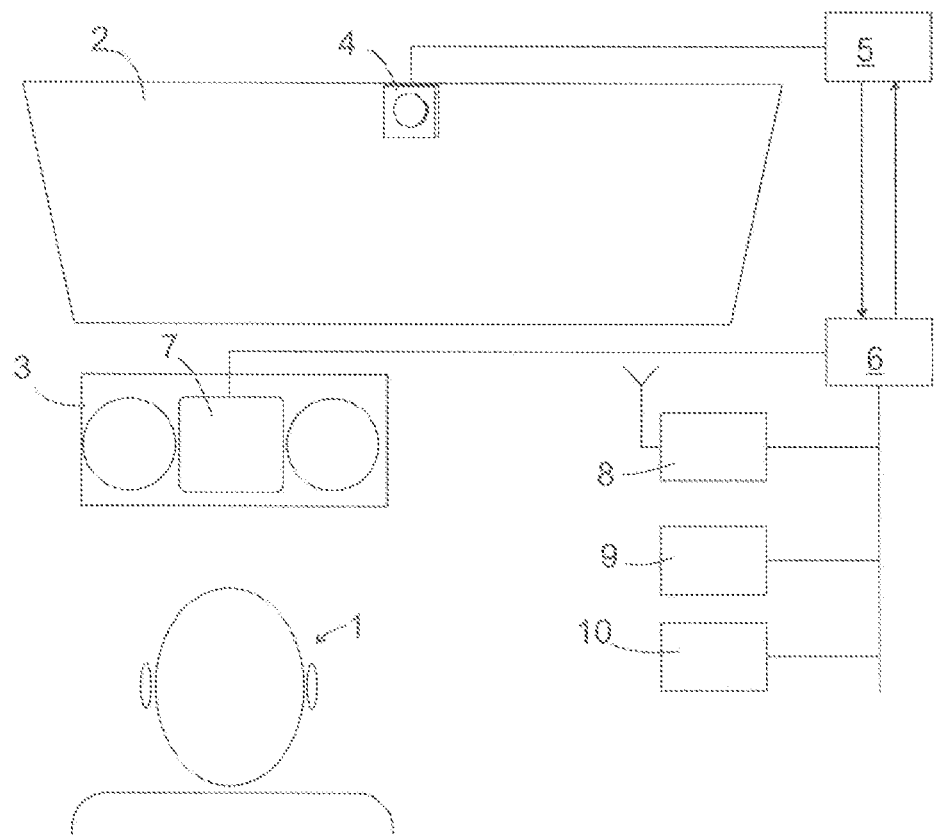
FIG. 1 shows a schematic partial view of a motor vehicle, in which the present disclosure is implemented.

FIG. 1 is a schematic view showing the driver 1 of a motor vehicle looking at the windscreen 2 and at a display instrument 3 on the dashboard of the vehicle extending underneath the windscreen 2. A camera 4 is arranged on an upper edge of the windscreen 2, which camera observes the face of the driver 1 and in particular his eyes. The camera 4 is connected with an evaluation unit 5, which assesses the alertness of the driver 1 by means of the images supplied by the camera 4 in a manner explained further below. The evaluation unit 5 is connected with a driver unit 6, which is configured to display changing messages, in particular alpha-numeric messages, in a central display field 7 of the display instrument 3. The driver unit 6 generates the messages based on information from various sources such as a vehicle navigation system 8, a clock 9, a fuel level sensor 10 monitoring a tank containing operating fluids such as fuel, coolant, braking fluid or windscreen washer liquid, etc. The driver unit 6 includes a default set of messages from which it selects respectively one message, possibly supplemented by the current value of a variable such as the distance from an object external to the vehicle, or by an operating parameter of the vehicle or the like, for output in the display field 7.

Differences may be made between these messages due to various relevance classes. For a specific implementation of the present disclosure, not all of these relevance classes may occur or further classes may be defined beyond the classes mentioned below. A highest relevance class called Class A in the following may include messages which relate to the immediate environment of the vehicle and its momentary driving situation, such as the information derived from a respective radar sensor or the like that an overtaking vehicle is in a blind spot of the rear mirror, or the message derived from data of a vehicle navigation system indicating that the current speed of the vehicle is higher than admissible on the road on which the vehicle is currently travelling, etc. A lower relevance Class B may include messages relating to the time travelled or distance travelled since the last stop, the distance from tourist attractions or other interesting objects in the environment of the vehicle, the distance from a lay-by, a filling station or the like. A lower relevance Class C may for example include messages referring to operating parameters of the vehicle, for example the coolant temperature, the fuel tank level or the like, which may be worthwhile for the driver to know, but which are not anticipated to have any influence on his driving behavior. Messages of this kind may possibly progress into higher relevance Classes B or A if the parameter displayed in the messages approaches a threshold value or has already exceeded it. For example, a message referring to the temperature of the coolant or another temperature measured in the vehicle may be upgraded to a higher relevance class if the temperature has reached a level where its rise is due to an overload or a technical fault. A message relating to the fuel tank level should be upgraded to a higher relevance class if the fuel level has dropped below the minimum level. This may be a fixed specified value or, utilizing data of the vehicle navigation system 8, may be calculated as the anticipated fuel consumption until the time the next filling station is reached which lies along the planned driving route.

Figure 2:
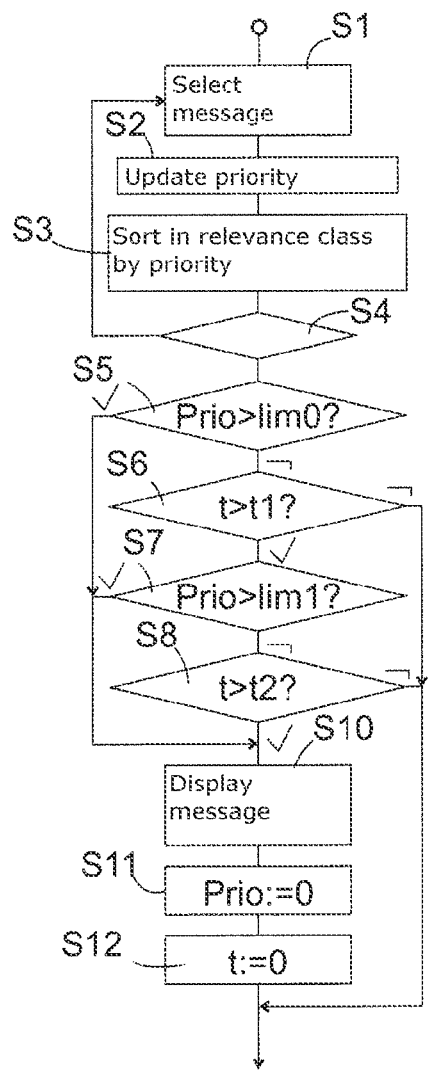
FIG. 2 shows a flow diagram of an operating method of the driver unit of FIG. 1 according to a first implementation of the present disclosure.

FIG. 2 shows a flow diagram of an operating method of the driver unit 6 according to a first implementation of the present disclosure. The shown method is repeated at time intervals which are distinctly shorter than a minimum waiting time t1 explained in more detail further below.

A memory of the driver unit 6 contains a directory of all messages which can be displayed in the display field 7. Each message has a relevance class and a priority value assigned to it. For a message selected in step S1 a priority value is updated in step S2. The manner in which the value is updated can be different from one message to the next. A message relating to the driving time since the last rest has a very low priority at a point in time t=0 directly following the rest, the value of which can be assumed to be 0, and this is illustrated by a graph M1 in FIG. 3. The priority increases linearly over time until it reaches a maximum and then remains constant until the drive is interrupted. The linear rise in priority as a function of the time can be approximated here in that for each iteration of the method in FIG. 2 the priority of the message is increased by a fixed increment until the maximum has been reached.

The priority of a message relating to the distance travelled since the last rest can be updated in an analog manner in that for each iteration of the method in FIG. 2 the priority is increased by an increment proportional to the driving speed.

Figure 3:
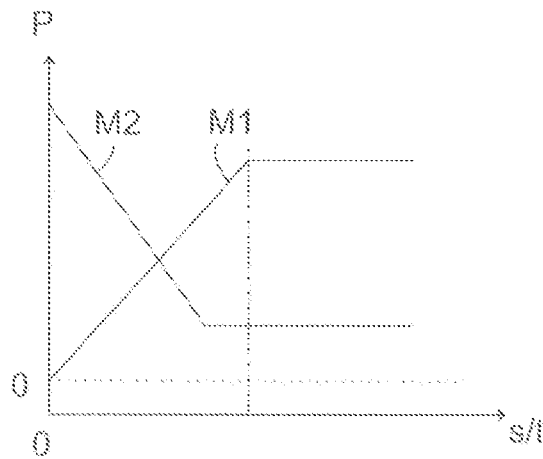
FIG. 3 shows examples for changing the priorities of messages over time or over a distance travelled by the vehicle.

Messages relating to the distance of the vehicle from an interesting object such as a tourist attraction, a rest area or lay-by, a filling station or similar, may include a priority of opposite dependency therefrom as shown by the graph M2 in FIG. 3. The priority increases with diminishing distance or diminishing driving time to the respective object; as the distance/driving time increases, the priority decreases and finally remains constant at a low value.

As can be recognized in FIG. 2 different messages may include maximum and minimum priority values which are different from each other.

Figure 4:
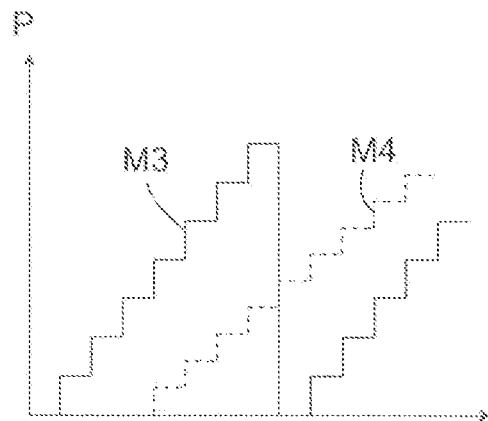
FIG. 4 shows the change in priorities of other messages when a message is displayed, respectively.

For messages of the lowest relevance Class C, updating may consist in that the priority value is increased by a fixed increment whenever a message has previously been output to the display field 7. The increments, as shown in FIG. 4 by way of the graph M3, M4, may be different from one message to the next.

For messages of the highest relevance Class A updating the priority consists in checking whether the message is applicable or not, and depending on this assessment, assigning a high priority or priority 0. A high priority should be assumed for the above mentioned examples if a vehicle happens to be in a blind spot or when a specified maximum speed has been exceeded.

If it is determined in step S4 that there is still a message whose priority has not been updated, steps S1 to S3 are repeated for this message, otherwise a number of checks follows for making a decision as to whether a new message should be output to the display field 7 or not. In the example discussed here, the first step S5 checks whether the highest priority message of relevance Class A includes a priority above a threshold value lim0. If yes, the method jumps directly to step S10 in order to display this message. Messages of Class A can thus be displayed at any time if they are applicable. If no applicable Class A message exists, it is checked in step S6 whether a minimum waiting time t1 has passed since the last output of a message to the display field 7. If this is not the case, the method ends without a message being issued. In this way it is avoided that the driver is swamped with messages, which could lead to him ignoring the messages, and an assessment of driver alertness based on the assessment of his reaction to the messages, would then be unreliable.

Alternatively the sequence of steps S5, S6 could be reversed with the result that following the output of a message to the display field 7, Class A messages would not be output again until after the minimum waiting time t1 has passed.

When the minimum waiting time t1 has passed it is checked in step S7, whether there is a message among the respectively highest priority messages the priority of which exceeds a threshold value lim1. If this is the case, the method jumps to step S10 in order to output the respective message on the display field 7.

Otherwise it is checked in step S8, whether since the last output of a message a maximum waiting time t2 has passed. If this is not the case the method ends, or the highest priority message among all messages is selected and displayed in step S10. The time delay between two switch-over times of the display field 7 can therefore never be greater than t2. In this way it is ensured that the time delay between two assessments of driver alertness cannot become greater than t2.

Assessment of driver alertness is performed in that the evaluation unit 5 determines, in a manner known as such, the viewing direction of the driver from the images of the camera 4 and checks how quickly after a switch-over of the display field 7 to a new message, the driver looks at the display field 7. A long reaction time or the absence of a reaction to the switch-over are indicators of a lack of alertness of the driver and trigger staggered reactions of the vehicle with the aim to restore alertness. These measures may be acoustic, optical or haptic warning signals which increase in intensity if alertness is repeatedly assessed as being insufficient. In the absence of a reaction of the driver to the warning signals the vehicle may even be brought to a standstill.

After a message has been displayed in step S10, the priority of the message is reset to 0 in step S11, as shown in FIG. 4 by the example of graph M3, in order to ensure that the same message does not appear again when step S10 is executed in a subsequent iteration of the method, and therefore a change occurs in the display field 7 which is perceptible to the driver 1. The different increments of the graphs M3, M4 shown in FIG. 4 lead to the corresponding messages needing times of different lengths in order, once they have been displayed, to reach the priority necessary for renewed display. In this way the messages are prevented from being cyclically repeated. Since the driver cannot predict which message will appear next, he must, when a change occurs in the display field 7, look at the display field 7 in order to take note of the newly displayed message and thereby involuntarily supplies the data necessary for assessing his alertness.

Together with the switch-over of the display field 7 to the new message the time t is reset to 0 in step 12, in order to execute the comparison with t1 and t2 in subsequent iterations of the method.

Figure 5:
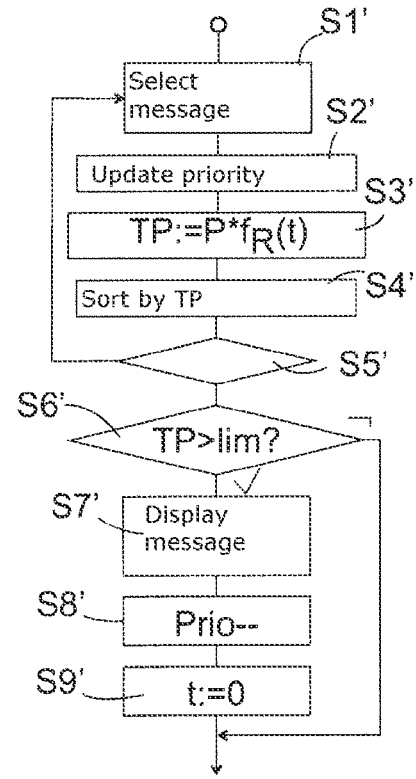
FIG. 5 shows a flow diagram of an operating method according to a second implementation of the present disclosure.
Figure 6:
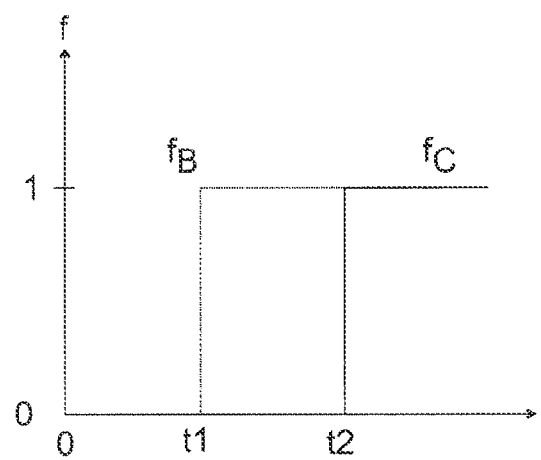
FIG. 6 shows the development over time, of weighting functions used in the method of FIG. 5.

FIG. 5 is a flow diagram of an alternative working method of the driver unit 6. This method too is periodically repeated in short time intervals. It differs from the method in FIG. 2 because of the use of two priority variables, an abstract priority P which corresponds to the priority used in the method of FIG. 2 and is updated in steps S1', S2' as described above with reference to FIG. 2, and a time-weighted priority TP which is obtained in step S3' from the abstract priority 0 of a message by multiplication with a weighting function $f_R(t)$. R denotes the relevance class and thus can in the example considered here assume the values A, B, C, and t denotes the time elapsed since outputting the last message. As shown in FIG. 6

$$f_B(t) = \begin{cases} 0 & \text{for } 0 \leq t < t1 \\ 1 & \text{for } t1 \leq t \end{cases}$$

$f_A$ may be constantly $=1$ or $=f_B$.

$$f_C(t) = \begin{cases} 0 & \text{for } 0 \leq t < t2 \\ 1 & \text{for } t2 \leq t \end{cases}$$

In step S4' the messages are sorted according to their time-weighted priority TP in a queue. Steps S1' to S4' are repeated until it is determined in step S5' that the priorities of all messages have been updated; than it is checked in step S6' whether the time-weighted priority TP of the highest priority message is high enough in order for it to be displayed. If it is not, the method ends, otherwise the respective message is displayed in step S7'.

When $f_A=1$, messages of relevance class A can be displayed at any time; if $f_B$ includes the progression shown in FIG. 6 and $f_A=f_B$, messages of relevance classes A, B are displayed at the earliest after the minimum waiting time t1, respectively. If during the time from t1 to t2 no message of these classes reaches the priority necessary for display, messages of class C may be displayed at the time t2, wherein, if this class contains more than one message, it can be ensured by a suitable selection of increments that a message of this class indeed exists at the time t2, which has the priority TP necessary for display, so that t2 indeed represents the highest possible waiting time between two switch-overs of the display field 7.

Steps S8', S9' of the method according to FIG. 5 are equal to steps S11, S12 of the method according to FIG. 2 and therefore do not need to be explained again.

While at least one exemplary embodiment has been presented in the foregoing detailed description, it should be appreciated that a vast number of variations exist. It should also be appreciated that the exemplary embodiment is only an example, and are not intended to limit the scope, applicability, or configuration of the present disclosure in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the present disclosure as set forth in the appended claims and their legal equivalents.

The invention claimed is:

1. A device for estimating the alertness of a driver in a moving vehicle comprising:
    a driver unit operably coupled to a display instrument and configured to switch over the display instrument in order to display a message relating to the movement of the vehicle; and
    an evaluation unit configured to assess the alertness of the driver on the basis of an eye movement of a driver's eyes in response to the switch-over relating to the message displayed.

2. The device according to claim 1, further comprising a camera configured to detect the eye movement of the driver in response to the switch-over.

3. The device of claim 1, wherein the message is one of a plurality of messages;
    wherein the driver unit is configured to assign a priority to each of the plurality of messages;
    wherein the driver unit is configured to select a message with the highest priority as the message to be displayed on the display instrument when switching-over; and
    wherein the driver unit is configured to change the priority of the displayed message.

4. An image processing program stored on a non-transitory computer readable medium that comprises instructions which when executed on a computer enable the driver unit and the evaluation unit according to claim 1.

5. An image processing program stored on a non-transitory computer readable medium comprising an instruction set which when executed on a computer enable to execute a method for estimating the alertness of a driver in a moving vehicle comprising:
    switching over a display instrument in order to display a message relating to the movement of the vehicle;
    detecting an eye movement of a driver in reaction to the switching over the display instrument to the message; and
    assessing the alertness on the basis of the detected eye movement.

6. The program according to claim 5, wherein the message is one of a plurality of messages and the method further comprises:
    assigning a priority to each of the plurality of messages;
    selecting a message with the highest priority as the message to be displayed on the display instrument when switching over.

7. The program according to claim 6, wherein the method further comprises lowering the priority of the displayed message.

8. The program according to claim 6, wherein the priority of at least one of the plurality of messages not selected is incremented.

9. The program according to claim 6, wherein the priority of at least one of the plurality of messages not selected is raised proportionally to an elapsed time.

10. The program according to claim 6, wherein at least one of the plurality of messages refers to an object external to the vehicle and the priority of the message is increased as the distance between the vehicle and the object decreases.

11. The program according to claim 6, wherein at least one of the plurality of messages refers to an operating parameter of the vehicle and the priority of the message is increased as the distance of the operating parameter from a threshold value decreases.

12. The program according to claim 6, wherein at least one of the plurality of messages refers to an operating parameter of the vehicle and the priority of the message is increased as the distance of the operating parameter from a threshold value is exceeded.

13. The program according to claim 6, wherein the plurality of messages are divided into at least two different relevance classes and switching over the display instrument is repeated as soon as the priority of one message of the first relevance class has exceeded a threshold value (lim0) since the display instrument was previously switched over.

14. The program according to claim 6, wherein the plurality of messages are divided into at least two different relevance classes and switching over the display instrument is repeated as soon as the priority of one message of the first relevance class has exceeded a minimum waiting time (t1) has elapsed since the display instrument was previously switched over.

15. The program according to claim 5, wherein a minimum waiting time is maintained between two repetitions of switching over the display instrument.

16. The program according to claim 5, wherein switching over the display instrument is repeated after a maximum waiting time (t2) has elapsed.

17. The program according to claim 16, wherein switching over the display instrument prior to the maximum waiting time (t2) having elapsed when the priority of one of the messages exceeds a threshold value (lim1).

18. The program of claim 5, wherein the message is one of a plurality of messages and the method further comprises:
    assigning a priority to each of the plurality of messages;
    selecting a message with the highest priority as the message to be displayed on the display instrument when switching over; and
    changing the priority of the displayed message.

19. A non-transitory computer-readable medium comprising an instruction set for enabling a computer to execute a method for estimating the alertness of a driver in a moving vehicle comprising:
    switching over a display instrument in order to display a message relating to the movement of the vehicle;

detecting an eye movement of a driver in reaction to the switching over the display instrument to the message; and assessing the alertness on the basis of the detected eye movement.

20. The medium of claim 19, wherein the message is one of a plurality of messages and the method further comprises:
   assigning a priority to each of the plurality of messages;
   selecting a message with the highest priority as the message to be displayed on the display instrument when switching over; and
   changing the priority of the displayed message.

* * * * *